US006960689B2

(12) United States Patent
Emura et al.

(10) Patent No.: US 6,960,689 B2
(45) Date of Patent: Nov. 1, 2005

(54) METHOD FOR PREPARING NITROGEN-CONTAINING COMPOUNDS

(75) Inventors: Takashi Emura, Shizuoka (JP); Tsuyoshi Haneishi, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/954,605

(22) Filed: Oct. 1, 2004

(65) Prior Publication Data

US 2005/0075513 A1 Apr. 7, 2005

Related U.S. Application Data

(62) Division of application No. 10/296,925, filed as application No. PCT/JP01/04504 on May 29, 2001, now Pat. No. 6,803,472.

(30) Foreign Application Priority Data

May 29, 2000 (JP) ........................................ 2000-158525

(51) Int. Cl.$^7$ ..................... C07C 231/02; C07C 277/02; C07C 257/10; C07C 335/30; C07C 335/32
(52) U.S. Cl. ....................................... 564/233; 564/240
(58) Field of Search ................................ 564/238, 240

(56) References Cited

U.S. PATENT DOCUMENTS 511,975 A 5/1894 Boger et al.

FOREIGN PATENT DOCUMENTS

GB 1445 257 8/1976

OTHER PUBLICATIONS

Bambino, Frank et al., *Facite Synthesis of Protected Dipeptide Acids Containing C–Terminal α,α–Dialkyl Amino Acids*, Tetrahedron Letters, vol. 32, No. 28, pp. 3407–3408, Great Britain, 1991.

Dukat, Malgorzata et al., *Structure–Activity Relationships for the Binding of Arylpiperazines and Arylbiguanides at 5–HT$_3$ Serotonin Receptors*, Journal of Med. Chem., vol. 39, pp. 4017–4026, 1996.

Ruhland, T. et al., *Structurally Diverse 2,6–Disubstituted Quinoline Derivatives by Sold–Phase Synthesis*, Tetrahedron Letters, vol. 37, No. 16, pp. 2757–2760, 1996, Great Britain.

Tssui, Kiyoshi et al., *Studies on Anti–inflammatory Agents. IV.[1)]Synthesis and Pharmacological Properties of 1,5–Diarylpyrazoles and Related Derivatives*, Chem. Pharm. Bulletin, vol. 45(6), pp. 987–995, Jan. 1997.

Wang, Wei–Bo et al., *Tin (II) Amides: New Reagents for the Conversion of Esters to Amides*, Journal of Org. Chem., vol. 57 pp. 6101–6103, 1992.

*Primary Examiner*—Peter O'Sullivan
(74) *Attorney, Agent, or Firm*—Browdy and Neimark, PLLC

(57) ABSTRACT

A synthesis method which comprises reacting NH group-containing compounds with thiocyanates, cyanamides, nitrites or esters in the presence of a silylating agent to synthesize the corresponding nitrogen-containing addition or substitution products. This method not only enables the direct and efficient synthesis of nitrogen-containing compounds including isothioureas, guanidines, amidines and amides, but it also has a wide range of applications and is suitable for large-scale synthesis.

8 Claims, No Drawings

METHOD FOR PREPARING NITROGEN-CONTAINING COMPOUNDS

RELATED APPLICATIONS

This is a divisional of application Ser. No. 10/296,925, nationalized Nov. 29, 2002, now U.S. Pat. No. 6,803,472, which application is the national phase of international application PCT/JP01/04504, filed May 29, 2001.

TECHNICAL FIELD

The present invention relates to a novel method for preparing nitrogen-containing compounds (e.g., isothioureas, guanidines, amidines, amides) using amines.

BACKGROUND ART

Nitrogen-containing compounds including isothioureas, guanidines, amidines and amides are extremely important in the fields of pharmaceutical or agricultural synthesis. Typical techniques used for preparing these compounds from amines in a single step are shown below.

No technique is known to allow the direct synthesis of isothioureas from amines and thiocyanates.

A technique for synthesizing guanidines from amines and cyanamides is known from J. Med. Chem., 1996, 39, 4017, which reports reaction conditions involving heating the reaction mixture to 180° C. in concentrated hydrochloric acid.

A technique for synthesizing amidines from amines and nitrites is known from Chem. Pharm. Bull., 1997, 45, 987, which reports reaction conditions involving heating the reaction mixture to 150° C. in the presence of aluminum chloride.

A technique for synthesizing amides from amines and esters is known from Tetrahedron Lett., 1996, 37, 2757, which reports the use of trimethylaluminum for the synthesis. Also, another synthesis technique using a silylating agent is known from Tetrahedron Lett., 1991, 32, 3407, which reports the use of trimethylsilyl chloride for the synthesis. However, in these techniques, the silylating agent is used for the protection of other functional groups and does not appear to enhance the synthesis reaction because the esters to be amidated are reactive enough to easily react with the amines in the absence of the silylating agent. It is therefore impossible to predict from these techniques that the silylating agent enhances the amidation reaction of less reactive esters. Still another technique using tin bishexamethylsilylamide is known from J. Org. Chem., 1992, 57, 6101. However, this technique is based on a concept distinct from that of the synthesis reaction under consideration because the active species is tin.

These conventional techniques require the use of highly reactive metal compounds and/or extreme reaction conditions for the direct synthesis of nitrogen-containing compounds (e.g., isothioureas, guanidines, amidines, amides) from amines. Such conventional techniques are therefore unable to have a wide range of applications and have been unsuitable for large-scale synthesis in terms of running costs, energy consumption and environmental impact. In view of the foregoing, there has been a demand to develop a preparation method that is available for a wider range of applications and that allows the efficient preparation of nitrogen-containing compounds including isothioureas, guanidines, amidines and amides under mild reaction conditions.

DISCLOSURE OF THE INVENTION

As a result of our research efforts directed to overcoming the problems stated above, we found that the use of a silylating agent for catalyzing the reactions between NH group-containing compounds (e.g., amines) and thiocyanates, cyanamides, nitrites or esters enabled the direct and efficient synthesis of nitrogen-containing compounds of interest under mild reaction conditions. We also found that this synthesis technique using a silylating agent had a wide range of applications and was suitable for large-scale synthesis. The present invention has been accomplished on the basis of these findings.

In short, the present invention provides a method for preparing isothioureas, guanidines, amidines or amides, which comprises reacting a NH group-containing compound with a compound selected from the group consisting of thiocyanates, cyanamides, nitrites and esters (excluding highly reactive esters) in the presence of a silylating agent.

Also, the present invention provides a method for preparing isothioureas and/or tautomers thereof, in which a NH group-containing compound of general formula (I-A):

$R^{1a}R^{2a}NH$          (I-A)

wherein
$R^{1a}$ and $R^{2a}$, which are the same or different, each represent a hydrogen atom or an optionally substituted monovalent hydrocarbon residue, or $R^{1a}R^{2a}N$ represents an optionally substituted monovalent cyclic hydrocarbon residue, is reacted with a thiocyanate compound of general formula (II-A):

$R^{3a}SCN$          (II-A)

wherein
$R^{3a}$, which is the same or different, represents a hydrogen atom or an optionally substituted monovalent hydrocarbon residue, in the presence of a silylating agent and, if necessary, in the presence of an acid and/or a base to give an isothiourea compound of general formula (III-A) and/or a tautomer thereof:

wherein
$R^{1a}$, $R^{2a}$ and $R^{3a}$ are as defined above.

Further, the present invention provides a method for preparing guanidines and/or tautomers thereof, in which a NH group-containing compound of general formula (I-B):

$R^{1b}R^{2b}NH$          (I-B)

wherein
$R^{1a}$ and $R^{2b}$, which are the same or different, each represent a hydrogen atom or an optionally substituted monovalent hydrocarbon residue, or $R^{1b}R^{2b}N$ represents an optionally substituted monovalent cyclic hydrocarbon residue, is reacted with a cyanamide compound of general formula (II-B):

$R^{3b}R^{4b}NCN$          (II-B)

wherein $R^{3b}$ and $R^{4b}$, which are the same or different, each represent a hydrogen atom or an optionally substituted monovalent hydrocarbon residue, or $R^{3b}R^{4b}N$ represents an optionally substituted monovalent cyclic hydrocarbon residue, in the presence of a silylating agent and, if necessary, in the presence of an acid and/or a base to give a guanidine compound of general formula (III-B) and/or a tautomer thereof:

(III-B)

wherein
$R^{1b}$, $R^{2b}$, $R^{3b}$ and $R^{4b}$ are as defined above.

In addition, the present invention provides a method for preparing amidines and/or tautomers thereof, in which a NH group-containing compound of general formula (I-C):

$R^{1c}R^{2c}NH$      (I-C)

wherein
$R^{1c}$ and $R^{2c}$, which are the same or different, each represent a hydrogen atom or an optionally substituted monovalent hydrocarbon residue, or $R^{1c}R^{2c}N$ represents an optionally substituted monovalent cyclic hydrocarbon residue, is reacted with a nitrile compound of general formula (II-C):

$R^{3c}CN$      (II-C)

wherein
$R^{3c}$ represents a hydrogen atom or an optionally substituted monovalent hydrocarbon residue, in the presence of a silylating agent and, if necessary, in the presence of an acid and/or a base to give an amidine compound of general formula (III-C) and/or a tautomer thereof:

(III-C)

wherein
$R^{1c}$, $R^{2c}$ and $R^{3c}$ are as defined above.

Furthermore, the present invention provides a method for preparing amides, in which a NH group-containing compound of general formula (I-D):

$R^{1d}R^{2d}NH$      (I-D)

wherein
$R^{1d}$ and $R^{2d}$, which are the same or different, each represent a hydrogen atom or an optionally substituted monovalent hydrocarbon residue, or $R^{1d}R^{2d}N$ represents an optionally substituted monovalent cyclic hydrocarbon residue, is reacted with an ester compound (excluding highly reactive esters) of general formula (II-D):

$R^{3d}CO_2R^{4d}$      (II-D)

wherein
$R^{3d}$ represents a hydrogen atom or an optionally substituted monovalent hydrocarbon residue, $R^{4d}$ represents a hydrogen atom, an optionally substituted monovalent hydrocarbon residue or a substituted silyl group, or $R^{3d}CO_2R^{4d}$ represents an optionally substituted cyclic hydrocarbon, in the presence of a silylating agent and, if necessary, in the presence of an acid and/or a base to give an amide compound of general formula (III-D):

(III-D)

wherein
$R^{1d}$, $R^{2d}$ and $R^{3d}$ are as defined above.

BEST MODE FOR CARRYING OUT THE INVENTION

The method of the present invention can be applied where NH group-containing compounds are reacted with thiocyanates, cyanamides, nitriles or esters to synthesize nitrogen-containing addition or substitution products thereof.

As used herein, a NH group-containing compound literally refers to any compound containing NH, including a linear or cyclic primary amine, a linear or cyclic secondary amine and a linear or cyclic imide.

As used herein, thiocyanates, cyanamides, nitrites and esters are intended to include, for example, compounds represented by general formulae (II-A), (II-B), (II-C) and (II-D), respectively.

As used herein, isothioureas, guanidines, amidines and amides are intended to include, for example, compounds represented by general formulae (III-A), (III-B), (III-C) and (III-D), respectively. According to the present invention, these isothioureas, guanidines, amidines and amides are obtained through the addition or substitution reactions of NH group-containing compounds with thiocyanates, cyanamides, nitrites and esters, respectively. More specifically, isothioureas are derived from thiocyanates, guanidines are derived from cyanamides, amidines are derived from nitrites, and amides are derived from esters.

According to the present invention, the nitrogen-containing compounds including isothioureas, guanidines, amidines and amides can be synthesized as follows.

Preparation of Isothioureas

A compound of general formula (I-A):

$R^{1a}R^{2a}NH$      (I-A)

wherein
$R^{1a}$ and $R^{2a}$, which are the same or different, each represent a hydrogen atom or an optionally substituted monovalent hydrocarbon residue, or $R^{1a}R^{2a}N$ represents an optionally substituted monovalent cyclic hydrocarbon residue, can be reacted with a compound of general formula (II-A):

$R^{3a}SCN$      (II-A)

wherein
$R^{3a}$ represents a hydrogen atom or an optionally substituted monovalent hydrocarbon residue, in an inert solvent or without using a solvent in the presence of a silylating agent and, if necessary, in the presence of an acid and/or a base to give an isothiourea compound of general formula (III-A) and/or a tautomer thereof:

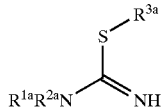
(III-A)

wherein
$R^{1a}$, $R^{2a}$ and $R^{3a}$ are as defined above.

The tautomer as used herein refers to a compound of general formula (III-A'):

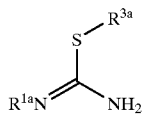
(III-A')

which may be generated when $R^{2a}$ in general formula (III-A) is a hydrogen atom. Exactly the same can be said for the case where $R^{1a}$ in general formula (III-A) is a hydrogen atom.

Preparation of Guanidines

A compound of general formula (I-B):

$R^{1b}R^{2b}NH$ (I-B)

wherein
$R^{1b}$ and $R^{2b}$, which are the same or different, each represent a hydrogen atom or an optionally substituted monovalent hydrocarbon residue, or $R^{1b}R^{2b}N$ represents an optionally substituted monovalent cyclic hydrocarbon residue, can be reacted with a compound of general formula (II-B):

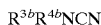
$R^{3b}R^{4b}NCN$ (II-B)

wherein
$R^{3b}$ and $R^{4b}$, which are the same or different, each represent a hydrogen atom or an optionally substituted monovalent hydrocarbon residue, or $R^{3b}R^{4b}N$ represents an optionally substituted monovalent cyclic hydrocarbon residue, in an inert solvent or without using a solvent in the presence of a silylating agent and, if necessary, in the presence of an acid and/or a base to give a guanidine compound of general formula (III-B) and/or a tautomer thereof:

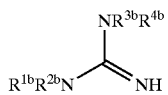
(III-B)

wherein
$R^{1b}$, $R^{2b}$, $R^{3b}$ and $R^{4b}$ are as defined above.

The tautomer as used herein refers to a compound of general formula (III-B') or (III-B''):

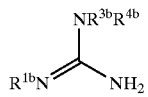
(III-B')

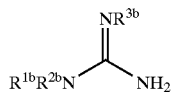
(III-B'')

which may be generated when $R^{2b}$ or $R^{4b}$ in general formula (III-B) is a hydrogen atom. Exactly the same can be said for the case where $R^{1b}$ or $R^{3b}$ in general formula (III-B) is a hydrogen atom.

Preparation of Amidines

A compound of general formula (I-C):

$R^{1c}R^{2c}NH$ (I-C)

wherein
$R^{1c}$ and $R^{2c}$, which are the same or different, each represent a hydrogen atom or an optionally substituted monovalent hydrocarbon residue, or $R^{1c}R^{2c}N$ represents an optionally substituted monovalent cyclic hydrocarbon residue, can be reacted with a compound of general formula (II-C):

$R^{3c}CN$ (II-C)

wherein
$R^{3c}$ represents a hydrogen atom or an optionally substituted monovalent hydrocarbon residue, in an inert solvent or without using a solvent in the presence of a silylating agent and, if necessary, in the presence of an acid and/or a base to give an amidine compound of general formula (III-C) and/or a tautomer thereof:

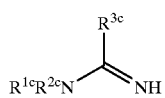
(III-C)

wherein
$R^{1c}$, $R^{2c}$ and $R^{3c}$ are as defined above.

The tautomer as used herein refers to a compound of general formula (III-C'):

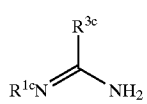
(III-C')

which may be generated when $R^{2c}$ in general formula (III-C) is a hydrogen atom. Exactly the same can be said for the case where $R^{1c}$ in general formula (III-C) is a hydrogen atom.

Preparation of Amides

A compound of general formula (I-D):

$R^{1d}R^{2d}NH$ (I-D)

wherein
$R^{1d}$ and $R^{2d}$, which are the same or different, each represent a hydrogen atom or an optionally substituted monovalent hydrocarbon residue, or $R^{1d}R^{2d}N$ represents an optionally substituted monovalent cyclic hydrocarbon residue,
can be reacted with an ester compound (excluding highly reactive esters) of general formula (II-D):

$$R^{3d}CO_2R^{4d} \quad (II\text{-}D)$$

wherein
R$^{3d}$ represents a hydrogen atom or an optionally substituted monovalent hydrocarbon residue, R$^{4d}$ represents a hydrogen atom, an optionally substituted monovalent hydrocarbon residue or a substituted silyl group, or R$^{3d}CO_2R^{4d}$ represents an optionally substituted cyclic hydrocarbon,
in an inert solvent or without using a solvent in the presence of a silylating agent and, if necessary, in the presence of an acid and/or a base to give an amide compound of general formula (III-D):

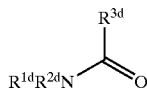

(III-D)

wherein
R$^{1d}$, R$^{2d}$ and R$^{3d}$ are as defined above.

As used herein, highly reactive esters are intended to mean active compounds capable of reacting with amines in the absence of a particular catalyst to yield the corresponding amides. Examples include compounds of general formula (II-D) wherein R$^d$ is pentafluorophenyl or paranitrophenyl. Preparation methods using such ester compounds are not intended to be within the scope of the present invention. The conditions under which these four types of reactions occur will be described below in more detail.

Examples of an inert solvent include hexane, cyclohexane, benzene, toluene, diethyl ether, diisopropyl ether, tert-butyl methyl ether, tetrahydrofuran, dioxane, dichloromethane, 1,2-dichloroethane and chloroform. Preferred for use are dichloromethane, 1,2-dichloroethane, benzene and toluene, or mixtures thereof.

The reaction may be performed at a temperature ranging from −78° C. to the boiling point of the reaction mixture, preferably −20° C. to 110° C.

Examples of the silylating agent available for use include those which are represented by the following formulae: R$^a$R$^b$R$^c$SiX, R$^a$R$^b$R$^c$SiOCOR$^d$, R$^a$R$^b$R$^c$SiOSO$_2$R$^d$, R$^a$R$^b$Si(OSO$_2$R$^d$)$_2$, (R$^a$R$^b$R$^c$SiO)$_{3-n}$X$_n$PO, (R$^a$R$^b$R$^c$Si)R$^f$NCOR$^g$, (R$^a$R$^b$R$^c$SiO)NR$^i$R$^j$ and (R$^a$R$^b$R$^c$Si)(R$^a$R$^b$R$^c$SiN) CR$^k$, wherein R$^a$, R$^b$ and R$^c$, which are the same or different, each represent an optionally substituted linear, branched or cyclic C$_1$–C$_{10}$ alkyl group, an optionally substituted phenyl group or a halogen atom; X represents a halogen atom; R$^d$ represents a hydrogen atom, an optionally substituted linear, branched or cyclic C$_1$–C$_{10}$ alkyl group, an optionally substituted phenyl group, a halogen atom or R$^a$R$^b$R$^c$SiO; n is 0, 1 or 2; R$^f$ represents R$^a$R$^b$R$^c$Si, a hydrogen atom, an optionally substituted linear, branched or cyclic C$_1$–C$_{10}$ alkyl group or an optionally substituted phenyl group; R$^g$ represents a hydrogen atom, an optionally substituted linear, branched or cyclic C$_1$–C$_{10}$ alkyl group, an optionally substituted phenyl group, R$^a$R$^b$R$^c$SiO or (R$^a$R$^b$R$^c$Si)R$^f$N; R$^i$ and R$^j$, which are the same or different, each represent a hydrogen atom, an optionally substituted linear, branched or cyclic C$_1$–C$_{10}$ alkyl group, an optionally substituted phenyl group or R$^a$R$^b$R$^c$Si, or NR$^i$R$^j$ represents a ring-forming substituent; and R$^k$ represents a hydrogen atom, an optionally substituted linear, branched or cyclic C$_1$–C$_{10}$ alkyl group, an optionally substituted phenyl group or R$^a$R$^b$R$^c$SiO. These silylating agents may be commercially available or may be prepared in a known manner. Specific examples include Me$_3$SiCl (Me$_3$Si being hereinafter referred to as TMS), Et$_3$SiCl (Et$_3$Si being hereinafter referred to as TES), tBuMe$_2$SiCl (tBuMe$_2$Si being hereinafter referred to as TBS), Me$_2$PhSiCl, TMSO$_2$CCF$_3$, TESO$_2$CCF$_3$, TBSO$_2$CCF$_3$, TMSO$_3$SCl, (TMSO)$_2$SO$_2$, TMSO$_3$SCF$_3$, TESO$_3$SCF$_3$, TBSO$_3$SCF$_3$, (TMSO)$_3$PO, (TMSNH)$_2$CO, (TBSNH)$_2$CO, TMSNMeCHO, (TMS)$_2$NCHO, TMSNMeCOMe, (TMS)$_2$NCOMe, TMSNMeCOCF$_3$, TBSNMeCOCF$_3$, TMSNHCO$_2$TMS, (TMS)$_2$NH, (TMS)$_3$N, 1-TMSimidazole, 1-TBSimidazole, (TMSO)(TMSN)CMe, (TBSO)(TBSN)CMe and (TMSO)(TMSN)CCF$_3$, with TMSCl, (TMSO)$_2$SO$_2$, TMSO$_3$SCF$_3$, TESO$_3$SCF$_3$, TBSO$_3$SCF$_3$ and (TMSO)(TMSN)CMe being preferred. These agents may be used alone or in combination in an amount of 0.1 to 10 equivalents, preferable 1 to 4 equivalents, per amino group present in starting materials.

Further, the reaction may be performed in the presence of an acid and/or a base, if necessary. The acid may be any one of commonly-used Lewis acids and proton acids, or may be any one of inorganic acids (e.g., HCl, H$_2$SO$_4$, H$_3$PO$_4$) and organic acids (e.g., CF$_3$CO$_2$H, CF$_3$SO$_3$H, MeSO$_3$H). The base may be selected from inorganic bases (e.g., K$_2$CO$_3$, Na$_2$CO$_3$, KHCO$_3$, NaHCO$_3$), organic bases (e.g., pyridine, Et$_3$N, Et$_2$iPrN, N,N-dimethylaminopyridine) and organic metals (e.g., MeLi, nBuLi, sBuLi, tBuLi, MeMgCl, MeMgBr, EtMgCl, EtMgBr, iPrMgCl, iPrMgBr, tBuMgCl, tBuMgBr).

As used herein, the optionally substituted monovalent hydrocarbon residue as R$^{1a}$, R$^{2a}$, R$^{3a}$, R$^{1b}$, R$^{2b}$, R$^{3b}$, R$^{4b}$, R$^{1c}$, R$^{2c}$, R$^{3c}$, R$^{1d}$, R$^{2d}$, R$^{3d}$ and R$^{4d}$ refers to a saturated or unsaturated C$_1$–C$_{30}$ hydrocarbon residue which may be linear, branched or cyclic and may further contain a heterocyclic ring. Examples include:

alkyl groups such as methyl, ethyl, n-propyl, n-butyl, n-pentyl, n-hexyl, i-propyl, i-butyl, sec-butyl, tert-butyl, i-pentyl, neopentyl, tert-pentyl, i-hexyl, cyclopropyl, cyclopropylmethyl, cyclobutyl, 2-cyclobutylethyl, cyclopentyl, 1-cyclohexylnonyl, cycloheptyl and cyclooctyl;

alkenyl groups such as vinyl, 1-propenyl, 1-butenyl, 1-pentenyl, 1-hexenyl, allyl, 2-butenyl, 2-pentenyl, 2-hexenyl, 3-butenyl, 3-pentenyl, 3-hexenyl, 1-cyclopropenyl, 2-cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 1-cyclopropenyl, 1-methylvinyl, 1-methyl-1-cyclopropenyl, 1-methyl-3-cyclopentenyl, 3-methyl-2-pentenyl, 3-methyl-2-cyclohexenyl, 1-ethyl-1-hexenyl and 1-ethyl-2-cyclohexenyl;

alkynyl groups such as ethynyl, 1-propynyl, 1-butynyl, 1-pentynyl, 1-hexynyl, 2-propynyl, 2-butynyl, 2-pentynyl, 2-hexynyl, 3-butynyl, 3-pentynyl, 3-hexynyl, 1-methyl-2-propynyl, 3-methyl-1-butynyl, 1-ethyl-2-propynyl, 2-cyclooctynyl, 3-cyclodecynyl and 1-propyl-2-cyclotridecynyl; and aromatic groups such as phenyl, naphthyl, anthryl, phenanthryl and pyrenyl.

The heterocyclic ring refers to a saturated or unsaturated cyclic hydrocarbon containing one or more heteroatoms (e.g., nitrogen, oxygen, sulfur) as its ring members. Examples include aziridine, oxirane, thiirane, azetidine, oxetane, pyrrolidine, oxolane, thiolane, pyrrole, furan, thiophene, pyrazolidine, imidazoline, isoxazoline, oxazole, isothiazole, thiazole, pyridine, pyran, pyrimidine, pyrazine, indoline, benzofuran, benzothiophene, benzoxazole, chroman, isoquinoline, quinoxaline, carbazole and acridine.

As used herein, the cyclic hydrocarbon in the optionally substituted monovalent cyclic hydrocarbon residue as $R^{1a}R^{2a}N$, $R^{1b}R^{2b}N$, $R^{3b}R^{4b}N$, $R^{1c}R^{2c}N$ and $R^{1d}R^{2d}N$ refers to a saturated or unsaturated cyclic $C_1$–$C_{20}$ hydrocarbon which may contain, as its ring members, a heteroatom(s) in addition to the nitrogen atom. Examples include aziridine, azetidine, pyrrolidine, pyrrole, pyrazolidine, imidazoline, oxazolidine, isoxazolidine, isothiazolidine, piperazine, morpholine, indole, dihydroisoquinoline and carbazole.

As used herein, the substituent of the substituted silyl group as $R^{4d}$ refers to a linear, branched or cyclic $C_1$–$C_{10}$ alkyl group or a $C_6$–$C_{10}$ aryl group. Examples include methyl, ethyl, n-propyl, n-butyl, n-pentyl, n-hexyl, i-propyl, i-butyl, s-butyl, t-butyl, cyclohexyl and phenyl.

As used herein, the cyclic hydrocarbon as $R^{3d}CO_2R^{4d}$ refers to a saturated or unsaturated cyclic $C_2$–$C_{20}$ hydrocarbon which may contain, as its ring members, a heteroatom(s) in addition to the oxygen atoms. Examples include tetrahydro-2-furanone, tetrahydro-2-pyrone, coumarin, isocoumarin, 2(3H)-benzofuranone and phthalide.

As used herein, examples of the substituent of the optionally substituted monovalent hydrocarbon residue as $R^{1a}$, $R^{2a}$, $R^{3a}$, $R^{1b}$, $R^{2b}$, $R^{3b}$, $R^{4b}$, $R^{1c}$, $R^{2c}$, $R^{3c}$, $R^{1d}$, $R^{2d}$, and $R^{3d}$ include a halogen atom, —$SiR^eR^fR^g$, —$CONR^iR^j$, —$CO_2H$, —$NO_2$, —$N_3$, —$NR^mR^n$, —$OR^p$, =O, —$S(O)_nR^q$, =S and —$P(O)(OR^x)(OR^y)$. $R^e$, $R^f$ and $R^g$ in $SiR^eR^fR^g$ each represent a hydrogen atom, a halogen atom, a linear, branched or cyclic $C_1$–$C_5$ alkyl group or an optionally substituted $C_6$–$C_{15}$ phenyl group. Examples of a group represented by —$SiR^eR^fR^g$ include trimethylsilyl, triethylsilyl, t-butyldimethylsilyl, dimethylphenylsilyl and chlorodimethylsilyl.

$R^i$ and $R^j$ in $CONR^iR^j$ each represent a hydrogen atom or a saturated or unsaturated monovalent $C_1$–$C_{20}$ hydrocarbon residue which may have a substituent(s) at any position and may be linear, branched or cyclic and may further contain a heteroatom(s) or a heterocyclic ring, or $NR^iR^j$ represents a saturated or unsaturated cyclic $C_2$–$C_{20}$ hydrocarbon which may have a substituent(s) at any position. Examples of a group represented by $NR^iR_j$ include amino, methylamino, benzylamino, ethylamino, dimethylamino, ethylmethylamino, pyrrolidinyl, piperidino, morpholino, acetamide, benzamide, N-methylacetamide, benzamide, t-butoxycarbonylamino, N-methyl-t-butoxycarbonylamino, methylsulfonylamino, ethylsulfonylamino, propylsulfonylamino, isopropylsulfonylamino, butylsulfonylamino, isobutylsulfonylamino, phenylsulfonylamino, p-tolylsulfonylamino and p-chlorophenylsulfonylamino.

$R^m$ and $R^n$ in $NR^mR^n$ each represent a hydrogen atom or a saturated or unsaturated monovalent $C_1$–$C_{20}$ hydrocarbon residue which may have a substituent(s) at any position and may be linear, branched or cyclic and may further contain a heteroatom(s) or a heterocyclic ring, or $NR^mR^n$ represents a saturated or unsaturated cyclic $C_2$–$C_{20}$ hydrocarbon which may have a substituent(s) at any position. Examples of a group represented by $NR^mR^n$ include amino, methylamino, benzylamino, ethylamino, dimethylamino, ethylmethylamino, pyrrolidinyl, piperidino, morpholino, acetamide, benzamide, N-methylacetamide, benzamide, t-butoxycarbonylamino, N-methyl-t-butoxycarbonylamino, methylsulfonylamino, ethylsulfonylamino, propylsulfonylamino, isopropylsulfonylamino, butylsulfonylamino, isobutylsulfonylamino, phenylsulfonylamino, p-tolylsulfonylamino and p-chlorophenylsulfonylamino.

$R^p$ represents a hydrogen atom or a saturated or unsaturated monovalent $C_1$–$C_{20}$ hydrocarbon residue which may have a substituent(s) at any position and may be linear, branched or cyclic and may further contain a heteroatom(s) or a heterocyclic ring. Examples of such a hydrocarbon residue include methyl, isopropyl, t-butyl, benzyl, p-methoxybenzyl, p-methoxyphenyl, cyclopropylmethyl, methoxymethyl, ethoxymethyl, benzyloxymethyl, methylthiomethyl, ethylthiomethyl, methoxycarbonyl, tetrahydropyranyl, tetrahydrofuranyl, trimethylsilyl, triethylsilyl, t-butyldimethylsilyl and dimethylphenylsilyl.

In $S(O)_nR^q$, n is 0, 1 or 2 and $R^q$ represents a saturated or unsaturated monovalent $C_1$–$C_{20}$ hydrocarbon residue which may have a substituent(s) at any position and may be linear, branched or cyclic and may further contain a heteroatom(s) or a heterocyclic ring. Examples of such a hydrocarbon residue include methyl, ethyl, isopropyl, phenyl, p-tolyl, p-chlorophenyl and benzyl.

$R^x$ and $R^y$ in $P(O)(OR^x)(OR^y)$ each represent a hydrogen atom or a saturated or unsaturated monovalent $C_1$–$C_{20}$ hydrocarbon residue which may have a substituent(s) at any position and may be linear, branched or cyclic and may further contain a heteroatom(s) or a heterocyclic ring. Examples of such a hydrocarbon residue include methyl, ethyl, isopropyl, t-butyl, phenyl, p-tolyl, p-chlorophenyl, p-methoxyphenyl, benzyl, p-methoxybenzyl, methoxymethyl, tetrahydropyranyl and t-butyldimethylsilyl.

EXAMPLES

The present invention will be further described in the following examples. The examples are provided for illustrative purposes only, and are not intended to limit the scope of the invention.

Example 1

Synthesis of N-(5-(N-(S-ethylisothioureido))-2-(pyrrolidin-1-yl)benzyl)-2,2,2,-trifluoroacetamide N-(5-Amino-2-(pyrrolidin-1-yl)benzyl)-2,2,2,-trifluoroacetamide (109.3 mg) was dissolved in ethyl thiocyanate (328 µl). To this solution, trimethylsilyl trifluoromethanesulfonate (83 µl) and then trifluoromethanesulfonic acid (37 µl) were added dropwise at room temperature. After continued stirring for 3 hours at room temperature, saturated aqueous sodium bicarbonate was added to the solution, which was then extracted with chloroform. The extracted solution was dried over anhydrous sodium sulfate and evaporated under reduced pressure to remove the solvent. The resulting residue was purified by silica gel column chromatography (liquid phase: chloroform/methanol=50/1) to give the titled compound (134.1 mg, yield 94%).

1H-NMR (200 MHz, CDCl$_3$) δ: 1.356 (3H, t, J=7.4 Hz), 1.8–2.1 (4H, m), 2.8–3.2 (6H, m), 4.3–4.7 (4H, m), 6.7–6.9 (2H, m), 7.12 (1H, d, J=8.3 Hz), 8.8–9.2 (1H, br).

Example 2

Synthesis of N-(p-tolyl)-S-ethylisothiourea

To a solution of toluidine (106.5 mg) in dichloromethane (5 ml), trimethylsilyl trifluoromethanesulfonate (198 µl) and then ethyl thiocyanate (130.1 mg) were added dropwise at room temperature. After continued stirring overnight at room temperature, saturated aqueous sodium bicarbonate (1 ml) was added to the solution and further stirred. The dichloromethane layer separated from the above reaction mixture was dried over anhydrous sodium sulfate and concentrated under reduced pressure to give the titled compound (203.4 mg, yield 100%).

1H-NMR (200 MHz, CDCl$_3$) δ: 1.358 (3H, t, J=7.3 Hz), 2.310 (3H, s), 3.026 (2H, q, J=7.3 Hz), 3.7–4.3 (2H, br), 6.842 (2H, d, J=8.0 Hz), 7.118 (2H, d, J=8.0 Hz).

Example 3

Synthesis of N-p-totlylacetamide

To a solution of toluidine (12.8 mg) in dichloromethane (50 μl), trimethylsilyl trifluoromethanesulfonate (23.8 μl), ethyl acetate (23 μl) and then pyridine (10.6 μl) were added dropwise at room temperature. After continued stirring overnight at room temperature, saturated aqueous sodium bicarbonate (1 ml) was added to the solution and further stirred. The dichloromethane layer separated from the above reaction mixture was dried over anhydrous sodium sulfate and concentrated under reduced pressure to give the titled compound (18.7 mg, yield 100%).

1H-NMR (200 MHz, DMSO-d$_6$) δ: 2.011 (3H, s), 2.232 (3H, s), 7.075 (2H, d, J=8.3 Hz), 7.449 (2H, d, J=8.3 Hz), 9.82 (1H, brs).

Example 4

Synthesis of N-p-tolylpropylamidine

To a solution of toluidine (12.3 mg) in propionitrile (100 μl), trimethylsilyl trifluoromethanesulfonate (23.8 μl) was added dropwise at room temperature. After continued stirring for 1 day at room temperature, 2N aqueous sodium hydroxide was added to the solution, which was then extracted with ethyl acetate. The ethyl acetate layer was dried over anhydrous sodium sulfate and concentrated under reduced pressure to give the titled compound (18.9 mg, yield 93%).

1H-NMR (200 MHz, DMSO-d$_6$) δ: 1.098 (3H, t, J=7.57 Hz), 2.157 (2H, q, J=7.57 Hz), 2.232 (3H, s), 3.5–5.5 (1H, br), 6.674 (2H, d, J=8.3 Hz), 7.046 (2H, d, J=8.3 Hz).

Example 5

Synthesis of N-p-tolylguanidine

To a solution of toluidine (14.2 mg) in dichloromethane (50 μl), trimethylsilyl trifluoromethanesulfonate (26.4 μl) and then cyanamide (16.7 μl) were added at room temperature. After continued stirring overnight at room temperature, concentrated aqueous sodium hydroxide was added to the solution, which was then extracted with ethyl acetate. The ethyl acetate layer was dried over anhydrous sodium sulfate and concentrated under reduced pressure to give the titled compound (20.0 mg, yield 100%).

1H-NMR (200 MHz, DMSO-d$_6$) δ: 2.246 (3H, s), 5.0–5.9 (4H, br), 6.847 (2H, d, J=8.3 Hz), 7.085 (2H, d, J=8.3 Hz).

Mass (mass spectrometry) m/e: 149 (M+).

Example 6

Synthesis of N-benzyl-S-ethylisothiourea

Benzylamine (13.8 mg) was dissolved in ethyl thiocyanate (50 μl). To this solution, trimethylsilyl trifluoromethanesulfonate (25.7 μl) was added dropwise at room temperature. After continued stirring for 1 day at room temperature, 2N aqueous sodium hydroxide was added to the solution, which was then extracted with ethyl acetate. The ethyl acetate layer was dried over anhydrous sodium sulfate and concentrated under reduced pressure to give the titled compound (25.4 mg, yield 100%).

1H-NMR (200 MHz, DMSO-d$_6$) δ: 1.198 (3H, t, J=7.3 Hz), 2.855 (2H, q, J=7.3 Hz), 4.286 (2H, s), 6.2–6.9 (2H, br), 7.1–7.4 (5H, m).

Example 7

Synthesis of p-tolylamidine Hydrochloride

To a solution of hexamethyl disilazane (484 mg) in dichloromethane (1 ml), methanol (96 mg) was added dropwise at room temperature. After cooling on ice, trimethylsilyl trifluoromethanesulfonate (667 mg) was added dropwise to the solution. After the resulting suspension was stirred for 1 hour at room temperature, p-tolunitrile (351 mg) was added dropwise and further stirred for 2 nights at room temperature. The suspension was poured into 2N aqueous sodium hydroxide and extracted with dichloromethane. The extracted solution was dried over anhydrous sodium sulfate and evaporated under reduced pressure to remove the solvent. The resulting residue was purified by column chromatography on silica gel carrying amino groups (liquid phase: dichloromethane/methanol=5/1), followed by addition of 4N solution of hydrogen chloride in ethyl acetate and evaporation under reduced pressure to remove the solvent, thereby giving the titled compound (7 mg, yield 2%).

1H-NMR (270 MHz, DMSO-d$_6$) δ: 2.41 (3H, s), 7.43 (2H, d, J=8.0 Hz), 7.74 (2H, d, J=8.0 Hz), 9.06 (2H, s), 9.30 (2H, s).

Example 8

Synthesis of N-allyl-p-tolylamidine

To a solution of allylamine (171 mg) in p-tolunitrile (117 mg), trimethylsilyl trifluoromethanesulfonate (222 mg) was added dropwise at room temperature. After stirring for 2 nights at room temperature, 2N aqueous sodium hydroxide was added to the solution, which was then extracted with dichloromethane. The extracted solution was dried over anhydrous sodium sulfate and evaporated under reduced pressure to remove the solvent. The resulting residue was purified by column chromatography on silica gel carrying amino groups (liquid phase: dichloromethane/methanol=20/1) to give the titled compound (170 mg, yield 98%).

1H-NMR (270 MHz, CDCl$_3$) δ: 2.38 (3H, s), 2.50–6.50 (2H, br), 4.00 (2H, s), 5.18 (1H, d, J=10.2 Hz), 5.29 (1H, d, J=17.2 Hz), 5.94–6.08 (1H, m), 7.20 (2H, d, J=7.9 Hz), 7.48 (2H, d, J=7.9 Hz).

In the comparison example shown below, toluidine and ethyl thiocyanate were reacted in the presence of a Lewis acid (titanium tetrachloride) to prepare N-(p-tolyl)-S-ethylisothiourea. The comparison example was compared with Example 2 where a silylating agent was used for catalyzing the reaction.

Comparison Example

To a solution of toluidine (215.0 mg) in dichloromethane (5 ml), titanium tetrachloride (61 μl) and then ethyl thiocyanate (350 mg) were added dropwise at room temperature. After heating at reflux for 3 hours, saturated aqueous sodium bicarbonate (1 ml) was added to the solution and further stirred. The dichloromethane layer separated from the above reaction mixture was dried over anhydrous sodium sulfate and concentrated under reduced pressure to give the titled compound (177 mg, yield 45%).

Table 1 shows a comparison of yield between Comparison Example and Example 2. Table 1 indicates that the present invention enables the compounds of interest to be prepared in extremely higher yields than the reactions using conventional catalysts such as Lewis acids.

TABLE 1

|  | Yield |
| --- | --- |
| Comparison Example | 45% |
| Example 2 | 100% |

Industrial Applicability

The present invention achieves the direct and efficient synthesis of nitrogen-containing compounds including isothioureas, guanidines, amidines and amides, which are extremely important in the filed of pharmaceutical or agricultural synthesis. This synthesis technique is available for a wide range of applications and suitable for large-scale synthesis.

What is claimed is:

1. A method for preparing a guanidines, which comprises reacting a NH group-containing compound with a cyanamide in the presence of a silylating agent.

2. The method according to claim 1, wherein a NH group-containing compound of formula (I-B):

$$R^{1b}R^{2b}NH \quad \text{(I-B)}$$

wherein
$R^{1b}$ and $R^{2b}$, which are the same or different, each represents a hydrogen atom or an optionally substituted monovalent hydrocarbon residue, or $R^{1b}R^{2b}N$ represents an optionally substituted monovalent cyclic residue, is reacted with a cyanamide compound of formula (II-B):

$$R^{3b}R^{4b}NCN \quad \text{(II-B)}$$

wherein
$R^{3b}$ and $R^{4b}$, which are the same or different, each represents a hydrogen atom or an optionally substituted monovalent hydrocarbon residue, or $R^{3b}R^{4b}N$ represents an optionally substituted monovalent cyclic hydrocarbon residue, in the presence of a silylating agent and, if necessary, in the presence of an acid and/or a base to give a guanidine compound of formula (III-B) and/or a tautomer thereof:

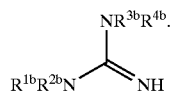

(III-B)

3. The method according to claim 1,
wherein the silylating agent comprises one or more of compounds represented by the following formulae: $R^aR^bR^cSiX$, $R^aR^bR^cSiOCOR^d$, $R^aR^bR^cSiOSO_2R^d$, $R^aR^bSi(OSO_2R^d)_2$, $(R^aR^bR^cSiO)_{3-n}X_nPO$, $(R^aR^bR^cSi)R^fNCOR^g$, $(R^aR^bR^cSi)NR^iR^j$ and $(R^aR^bR^cSiO)((R^aR^bR^cSiN)CR^k$,
wherein $R^a$, $R^b$ and $R^c$, which are the same or different, each represents an optionally substituted linear, branched or cyclic $C_1$–$C_{10}$ alkyl group, an optionally substituted phenyl group or a halogen atom;
X represents a halogen atom;
$R^d$ represents a hydrogen atom, an optionally substituted linear, branched or cyclic $C_1$–$C_{10}$ alkyl group, an optionally substituted phenyl group, a halogen atom or $R^aR^bR^cSiO$;
n is 0, 1 or 2;
$R^f$ represents $R^aR^bR^cSi$, a hydrogen atom, an optionally substituted linear, branched or cyclic $C_1$–$C_{10}$ alkyl group or an optionally substituted phenyl group;
$R^g$ represents a hydrogen atom, an optionally substituted linear, branched or cyclic $C_1$–$C_{10}$ alkyl group, an optionally substituted phenyl group, $R^aR^bR^cSiO$ or $(R^aR^bR^cSi)R^fN$;
$R^i$ and $R^j$, which are the same or different, each represent a hydrogen atom, an optionally substituted linear, branched or cyclic $C_1$–$C_{10}$ alkyl group, an optionally substituted phenyl group or $R^aR^bR^cSi$, or $NR^iR^j$ represents a ring-forming substituent; and
$R^k$ represents a hydrogen atom, an optionally substituted linear, branched or cyclic $C_1$–$C_{10}$ alkyl group, an optionally substituted phenyl group or $R^aR^bR^cSiO$.

4. The method according to claim 3, wherein the silylating agent comprises a compound represented by $R^aR^bR^cSiOSO_2CF_2R^d$.

5. The method according to claim 4, wherein the compound represented by $R^aR^bR^cSiOSO_2CF_2R^d$ is trimethylsilyl trifluoromethanesulfonate.

6. The method according to claim 2,
wherein the silylating agent comprises one or more of compounds represented by the following formulae: $R^aR^bR^cSiX$, $R^aR^bR^cSiOCOR^d$, $R^aR^bR^cSiOSO_2R^d$, $R^aR^bSi(OSO_2R^d)_2$, $(R^aR^bR^cSiO)_{3-n}X_nPO$, $(R^aR^bR^cSi)R^fNCOR^g$, $(R^aR^bR^cSi)NR^iR^j$ and $(R^aR^bR^cSiO)((R^aR^bR^cSiN)CR^k$,
wherein $R^a$, $R^b$ and $R^c$, which are the same or different, each represents an optionally substituted linear, branched or cyclic $C_1$–$C_{10}$ alkyl group, an optionally substituted phenyl group or a halogen atom;
X represents a halogen atom;
$R^d$ represents a hydrogen atom, an optionally substituted linear, branched or cyclic $C_1$–$C_{10}$ alkyl group, an optionally substituted phenyl group, a halogen atom or $R^aR^bR^cSiO$;
n is 0, 1 or 2;
$R^f$ represents $R^aR^bR^cSi$, a hydrogen atom, an optionally substituted linear, branched or cyclic $C_1$–$C_{10}$ alkyl group or an optionally substituted phenyl group;
$R^g$ represents a hydrogen atom, an optionally substituted linear, branched or cyclic $C_1$–$C_{10}$ alkyl group, an optionally substituted phenyl group, $R^aR^bR^cSiO$ or $(R^aR^bR^cSi)R^fN$;
$R^i$ and $R^j$, which are the same or different, each represent a hydrogen atom, an optionally substituted linear, branched or cyclic $C_1$–$C_{10}$ alkyl group, an optionally substituted phenyl group or $R^aR^bR^cSi$, or $NR^iR^j$ represents a ring-forming substituent; and
$R^k$ represents a hydrogen atom, an optionally substituted linear, branched or cyclic $C_1$–$C_{10}$ alkyl group, an optionally substituted phenyl group or $R^aR^bR^cSiO$.

7. The method according to claim 6, wherein the silylating agent comprises a compound represented by $R^aR^bR^cSiOSO_2CF_2R^d$.

8. The method according to claim 7, wherein the compound represented by $R^aR^bR^cSiOSO_2CF_2R^d$ is trimethylsilyl trifluoromethanesulfonate.

* * * * *